United States Patent [19]

Hyson

[11] 3,998,830
[45] Dec. 21, 1976

[54] PREPARATION OF BROMACIL/DIURON COMPLEX

[75] Inventor: Archibald Miller Hyson, Newark, Del.

[73] Assignee: E. I. Du Pont de Nemours and Company, Wilmington, Del.

[22] Filed: Apr. 1, 1975

[21] Appl. No.: 564,214

Related U.S. Application Data

[63] Continuation-in-part of Ser. No. 449,755, March 11, 1974, Pat. No. 3,914,230, which is a continuation-in-part of Ser. No. 159,547, July 2, 1971, abandoned, which is a continuation-in-part of Ser. No. 56,973, July 21, 1970, abandoned.

[52] U.S. Cl. .......................... 260/260; 260/96.5 R
[51] Int. Cl.$^2$ ....................... C07D 239/54
[58] Field of Search ...................... 260/260, 96.5 R

[56] References Cited

UNITED STATES PATENTS

| | | | |
|---|---|---|---|
| 3,235,357 | 2/1966 | Loux | 260/260 |
| 3,352,862 | 11/1967 | Loux | 260/260 |
| 3,914,122 | 10/1975 | Hyson | 260/260 |
| 3,914,230 | 10/1975 | Hyson | 260/260 |

*Primary Examiner*—Paul M. Coughlan, Jr.

[57] ABSTRACT

A herbicidal complex formed by the reaction of 1 mole of 5-bromo-3-sec-butyl-6-methyluracil with 1 mole of 3-(3,4-dichlorophenyl)-1,1-dimethylurea, and stable herbicidal formulations thereof.

6 Claims, No Drawings

PREPARATION OF BROMACIL/DIURON COMPLEX

CROSS-REFERENCE TO RELATED APPLICATION

This application is a continuation-in-part of my copending application Ser. No. 449,775, filed Mar. 11, 1974, U.S. Pat. No. 3,914,230, which is a continuation-in-part of my copending application Ser. No. 159,547, filed July 2, 1971, now abandoned, which is a continuation-in-part of my application Ser. No. 56,973, filed July 21, 1970, now abandoned.

BACKGROUND OF THE INVENTION

This invention is based on the discovery that 5-bromo-3-sec-butyl-6-methyluracil, hereinafter called bromacil, and 3-(3,4-dichlorophenyl)-1,1-dimethylurea, hereinafter called diuron, will react in a 1:1 molar ratio to form a complex which exists as a distinct chemical entity.

Bromacil and diuron have been known to the herbicidal art for many years and individually have been highly successful in herbicidal applications.

Because of the complementary nature of the activity of these herbicides it is desirable in some instances to employ both herbicides. It has now been discovered that a complex can be formed with enhanced formulation properties when compared with the formulation properties of physical mixtures of bromacil with diuron. It has also been observed that the bromacil/diuron complex nonetheless possesses the desired herbicidal activity one would expect to obtain with the use of bromacil and diuron as separate entities.

SUMMARY OF THE INVENTION

This invention relates to a complex consisting of one mole of bromacil combined with one mole of diuron.

This invention also relates to the method of forming a 1:1 molar complex of bromacil and diuron which is characterized in that bromacil and diuron are brought into intimate contact on a molecular level in such a way that the complexing reaction can substantially go to completion.

The bromacil and diuron can be brought together in intimate contact on the molecular level to form the complex by the following methods:

1. The bromacil and diuron can be dissolved in a common solvent and the bromacil/diuron complex isolated and the isolation from the common solvent can be by crystallization.
2. The bromacil and diuron can be melted together followed by solidification of the melt to yield the complex.
3. The bromacil and diuron in finely divided form can be slurried with water and heated with agitation to form the complex. Preferably, the slurry is heated to a temperature of at least 85° C. and the elevated temperature is maintained for at least 2 hours. Alternatively, somewhat lower temperatures and longer times can be employed.

Another aspect of this invention relates to stable agricultural compositions containing the bromaciydiuron complex of this invention as an active ingredient therein.

The preferred formulations contain an excess of either free bromacil or free diuron in addition to the complex. Particularly preferred formulations contain the bromacil and diuron in about 1:1 weight ratio or about a 2:1 weight ratio.

DESCRIPTION OF THE INVENTION

As indicated above this invention is based on the discovery that bromacil when combined with diuron on a molecular level will result in the formation of a distinct composition of matter herein referred to as a complex. This complex forms in a ratio of one mole of diuron for each mole of bromacil.

In general, any of the conventional techniques for achieving intimate contact known to those skilled in the art can be employed to form the complex. For example, the bromacil and diuron can be dissolved in a common solvent and crystallized to produce the complex. Alternatively, the bromacil and diuron can be melted together in a suitable vessel followed by solidification of the melt to produce the complex. The bromacil and diuron in finely divided form can be slurried with water and heated to form the complex. In all these methods, the conditions of time, temperature, solvent, and agitation must be chosen to cause the complexing to proceed substantially to completion.

The complex only forms between a 1:1 mole ratio of bromacil and diuron. If either of these materials is in excess of a 1:1 mole ratio the product obtained therefrom will consist of a mixture of the 1:1 mole complex and the ingredient that is in excess. Hereinafter, the use of the term bromacil/diuron complex will be used to refer to the 1:1 molar complex of the two components.

The conclusion that the bromacil/diuron complex is a separate and distinct chemical entity rather than a mere physical mixture of bromacil and diuron is supported by analytical and physical evidence. For example, a difference is noted in the X-ray diffraction pattern of the bromacil/diuron complex from either diuron or bromacil, thereby showing that the bromacil/diuron complex has a new and different crystalline structure.

In addition, a comparison of the infrared scans of the bromacil/diuron complex with infrared scans of the separate materials shows the appearance of several new bands at 3370 cm.$^{-1}$, 1608 cm.$^{-1}$ and 718 cm.$^{-1}$. Similarly, diuron has bands at 910 cm.$^{-1}$ and 630 cm.$^{-1}$ and bromacil has a band at 850 cm.$^{-1}$ that are not present in the infrared scan of the bromacil/diuron complex.

For example the melting point of the bromacil/diuron complex is sharp and is different from the melting point of the starting materials employed in preparing the complex.

This physical and analytical evidence, therefore, shows that the bromacil/diuron complex herein disclosed is a new chemical entity having a distinct melting point, a discrete crystalline habit and a different chemical structure than either unreacted bromacil, unreacted diuron or a physical mixture of the two materials.

The following examples are presented to further illustrate the method of preparing the bromacil/diuron complex of this invention.

EXAMPLE 1

233 Grams of diuron and 261 grams of bromacil (1:1 molar ratio) were dissolved in 2500 ml. of methanol by warming on the steam bath. The solution on standing overnight at room temperature deposited 323 g. of crystalline solid of m.p. 151°–153° C. After drying, the solids were examined by X-ray diffraction. The typical pattern associated with bromacil and diuron and disappeared and was replaced by a pattern indicating a new crystalline phase. When experiments were conducted with either bromacil or diuron at molar excess over the other, the X-ray pattern showed the presence of the new phase as well as that of the excess component.

EXAMPLE 2

23.3 Grams of diuron and 26.1 grams of bromacil were heated in an oven at a temperature of approximately 160° C. for one-half hour with occasional agitation to thoroughly blend the components. The resulting composition when cooled and allowed to crystallize contained the molar complex of bromacil and diuron as determined by X-ray diffraction.

As discussed above one aspect of this invention comprises physically stable herbicidal formulations containing as an active ingredient therein an herbicidally effective amount of the bromacil/diuron complex of this invention. The use of physical mixtures of bromacil and diuron in herbicidal compositions would result in formulation, storage and application problems. For example, ordinary powder formulations containing significant amounts of one of these two ingredients, such as 5–10% or more, plus an equal or greater amount of the other ingredient as a physical mixture, would lead to agglomeration and loss of dispersibility in storage. The use of the bromacil/diuron complex of this invention avoids these formulation, storage and application problems.

It will be understood that the terms "stable herbicidal formulation" and "physically stable herbicidal formulations" are used to describe compositions having a desirable shelf life, and that such non-liquid formulations will retain their free-flowing properties, their wettability, dispersibility and will remain free from caking during storage. The liquid formulation of this invention will retain fluidity, will avoid agglomeration of the discrete complex particles and will be capable of resuspension after storage when and if sedimentation should occur.

Therefore, the bromacil/diuron complex can be formulated into a variety of product forms which possess a degree of stability not obtainable when bromacil and diuron are combined as a physical mixture in similar formulations.

It will also be understood that the formulations of this invention can contain herbicides in addition to the bromacil/diuron complex of this invention. In some instances it may be desirable that the herbicide in addition to the complex is diuron or bromacil. However, it will be understood an excess of only one of diuron or bromacil can be added to any single formulation. The bromacil/diuron complex can be formulated as dusts containing 5 to 35% active ingredient, as wettable powders containing 25 to 90% active ingredient, and as high-strength concentrates containing 75 to 95% active ingredient. The bromacil/diuron complex can also be prepared as granules containing 5 to 50% active ingredient or as a suspension containing 15 to 50% active ingredient. In addition to the active ingredient, such formulations will contain wetting agents, dispersants, solid or liquid diluents, anticaking agents, antifoaming agents or other ingredients required to produce a commercially acceptable formulation. The amount and kind of additives selected for a formulation are determined by the end use of the product and the desired physical properties of the formulation.

The surface-active agents act as wetting, dispersing and emulsifing agents which assist dispersion of the active material in the spray, and improve wetting of waxy foliage and the like by the spray. The surfactants can include such anionic, non-ionic and cationic agents as have been used heretofore in pesticidal compositions of similar type. A detailed list of such agents may be found in "Detergents and Emulsifiers Annual", (John W. McCutcheon, Inc.).

Anionic and non-ionic surfactants are preferred. Among the anionic surfactants, preferred ones are alkali and alkaline earth salts of alkylarylsulfonic acids or alkali metal salts of dialkylsulfosuccinates. Non-ionic surfactants do not ionize in aqueous solution, but owe their solubility in water to hydrogen bonding groups such as ether oxygen or hydroxyl. Preferred non-ionic surfactants include polyoxyethylene esters of fatty acids and alkylphenylpolyethylene glycol ethers.

Preferred dispersants are alkali and alkaline earth salts of lignosulfonic acids, salts or polymerized alkylarylsulfonates which are sold under the "Daxad" and "Darvan" trademarks, as well as methylcellulose, polyvinyl alcohol and the like.

Surfactants are present in compositions of this invention in amounts up to about 20% by weight based on the total weight of the resulting composition. When larger amounts of surfactant are desired, as for improved wetting of, spreading of, or penetration into foliage, mixing in the spray tank is usually preferable for convenience.

Powder and dust preparations can be made by blending the active ingredient, with or without surfactant, with finely divided solids such as talcs, natural clays (kaolinites, attapulgites, etc.), pyrophyllite, diatomaceous earth; flours such as walnut shell, wheat, redwood, soya bean and cottonseed; or inorganic substances such as silica, silicates, magnesium carbonate, calcium carbonate, or sulfur. Other diluents such as anticaking or antifoaming agents may be required. The choice of the diluents will depend on the physical properties which are desired. The formulations are prepared by thoroughly blending the active ingredient with the other additives, and grinding in a hammer mill or similar device. The particle size for dust and powder preparations should be 50 microns or less in average diameter.

Powdered compositions can be converted to granules by adding a liquid, treating mechanically, and usually, drying. Mechanical devices such as granulating pans, mixers and extruders can be used. Compaction devices can be used without a liquid in the mixture. Water soluble binders, such as inorganic salts, urea, ligninsulfonates, methyl cellulose, and the like, can be included in these particulate formulations in amounts up to about 25% by weight of the finished granule or pellet. Such materials also aid in disintegration of the pellet and release of the active ingredient under field conditions. Alternatively, a solution, suspension, or melt of the active ingredient can be sprayed on the surface of preformed granules of clay, vermiculite, corn cob and the like. Surfactants may also be included in formulations of the latter type.

Suspension formulations can be made in water, or in organic solvents, or in mixtures of water and watermiscible organic solvents in which the active ingredient has a solubility under about 0.1%. The preparations usually include, in addition to the active ingredient and liquid carrier, surfactants, viscosity control agents, antimicrobial agents and other modifiers. They are prepared by grinding the components in a sand mill or pebble mill preferably until the average particle size is under 20 microns. Hydrocarbon and other flammable carriers should have boiling points above about 125° C. for safety in handling. Suspensions in hydrocarbons are suitable for extension in spray oils and, by inclusion of a suitable emulsifying agent, may also be made sprayable from water.

In order to increase the effectiveness of these formulations, other known herbicides may be added to a bromacil/diuron complex formulation. In some cases, the application of two or more herbicides at the same time is more effective than would be expected from the application of the individual compounds. The advantage can also be achieved by tank mixing different formulations, applying different granules or the like. The desired improved herbicidal effect may be obtained when the bromacil/diuron complex is applied with known herbicides in the following chemical classifications: substituted ureas, substituted triazines, phenols, carboxylic acids and their derivatives, inorganic and mixed inorganic-organic salts, and substituted uracils.

The bromacil/diuron complex is an effective herbicide for the control of undesired vegetation. It is effective against both broadleaf and grass weeds. It retains its activity in both heavy and sandy soils and it also retains its activity through a wide variety of climatic conditions. The precise amount of the complex needed to control weeds will vary according to the particular end result desired. The application rate is determined by the type of weeds to be controlled, the particular formulation used, the mode of application, the prevailing weather conditions, the local soil conditions and other factors. Broadly speaking, the application rate will be from about ¼ to about 40 kilograms of active ingredient per hectare. For selective weed control in crops, rates of ¼ to 12 kilograms of active ingredient per hectare can be used. The means of application for these materials will be standard for the types of formulations produced; that is, wettable powders can be mixed with water and sprayed in conventional equipment and granules can be applied in a conventional spreader. Therefore, in one embodiment of this invention weeds ordinarily occurring around trees in a citrus orchard are controlled by application of from 1 to 8 kilograms of bromacil/diuron complex per hectare of treated area. In another embodiment of this invention complete control of weeds in a tank farm and along a railroad right-of-way is obtained when a composition containing 35 kilograms of bromacil/diuron complex is applied per hectare of treated area. In a third embodiment weeds in pineapple are controlled by 1–12 kilograms per hectare.

The following examples are presented to further illustrate the formulation and application aspects of this invention. Parts and percentages in the following examples are by weight unless otherwise specified.

EXAMPLE 3

A mixture of technical grade diuron and technical grade bromacil in 1:1 weight ratio was co-melted together and the melt fed to a flaker to obtain the complex of diuron and bromacil along with some excess diuron. This composition was formulated as follows:

| | |
|---|---|
| composition described above | 50% |
| attapulgite | 41.5% |
| finely divided synthetic silica | 2% |
| basic magnesium carbonate | 2% |
| sodium lignin sulfonate | 1.5% |
| sodium alkylnaphthalene sulfonate | 3% |

The above ingredients were blended, hammer-milled to pass a 149 micron screen and reblended.

Eight kilograms of the above formulation are suspended in 600 liters of water and sprayed under a hectare of Hamlin oranges in Florida growing in a sandy loam soil. The treatment is directed so that it does not contact the citrus foliage and a minimum amount contacts the trunks of the trees. The treatment provides season long control of a large number of weeds including Bermudagrass (*Cynodon dactylon*), sandbur (Cenchrus spp.), crabgrass (Digitaria spp.), Florida pusley (*Richardia scabra*), barnyardgrass (*Echinochloa crusgalli*), natalgrass (*Rhynchelytrum repehs*), spanishneedles (*Bidens kipinnata*), pigweed (Amaranthus spp.), and annual nightshade (Solanum spp.).

EXAMPLE 4

An intimate mixture of technical grade diuron and technical grade bromacil in 1:2 weight ratio (excess bromacil) were melted together and fed to a flaker to obtain the complex of bromacil and diuron along with excess bromacil. This composition was formulated as follows:

| | |
|---|---|
| composition described above | 25.0% |
| kaolinite (Barden clay) | 65.5% |
| "Wyo-gel" bentonite | 4.0% |
| sodium lignin sulfonate | 2.0% |
| sodium alkylbenzenesulfonate | 1.0% |
| finely divided silica | 2.5% |

The above ingredients were blended and hammer-milled to a particle size essentially below 50 microns followed by reblending. Twenty kg. of the above composition (5 kg. active ingredient) are suspended in 400 l. of water and sprayed in a 6 meter band under established citrus trees in California. The treatment covers one half the total area, therefore the quantity prepared covers two hectares. The treatment provides control of Bermudagrass crabgrass, dandelion (*Taraxacum officinale*), goosegrass (*Eleusine inidica*), seedling Johnsongrass (*Sorghum halepense*) and lambsquarter (*Chenopodium album*), junglerice (*Echinochloa colonum*), puncturevine (*Tribulus terrestris*), pigweed (*Amaranthus spp.*), foxtail (setaria spp.), purslane (*Portulaca oleracea*), groundsel (senecio spp.), and fleabane (Erigeron spp.), as well as many other weeds.

EXAMPLE 5

| | |
|---|---|
| 1:1 bromacil-diuron complex from Ex. 1 | 80.0% |
| attapulgite | 11.5% |
| basic magnesium carbonate | 2.0% |
| finely divided synthetic silica | 2.0% |
| partially desulfonated sodium lignin sulfonate | 1.5% |
| sodium alkylnaphthalenesulfonate | 3.0% |

The above ingredients were blended, hammer-milled to pass a 149 micron screen and reblended.

Twenty-five kg. of the above formulation are suspended in 300 liters of water and sprayed on one hectare of area around a tank farm. The treatment controls all vegetation for an extended period.

The active ingredients shown in Examples 3 and 4 can similarly be formulated as 80% wettable powder.

EXAMPLE 6

| 1:1 bromacil-diuron complex from Ex. 1 | 95.0% |
|---|---|
| trimethylnonyl polyethylglycol ether | 1.0% |
| finely divided synthetic silica | 4.0% |

The above ingredients were blended, hammer-milled to pass a 250 micron screen and reblended to give a high-strength composition suitable for direct spray application or for further formulation. The above formulation is suspended in water at the rate of 40 kg. per 600 l. of water containing 0.5% wetting agent. This suspension is used to treat a railroad right-of-way. This treatment kills all vegetation along the treated area and maintains a clear right-of-way for an extended period.

EXAMPLE 7

The wettable powder of Example 5 was tank mixed with 5 parts of trimethylnonyl polyethyleneglycol ether per part of active component and sprayed around sign and guard posts along a highway. The treatment kills all vegetation and maintains the treated area in a weed-free state for an extended period.

EXAMPLE 8

| 1:1 bromacil-diuron complex of Ex. 1 | 30.0% |
|---|---|
| calcium lignin sulfonate and wood sugars | 15.0% |
| sodium carbonate | 2.0% |
| hydrated attapulgite | 2.0% |
| sodium pentachlorophenate | 0.7% |
| water | 50.3% |

The dry components described above were ground to pass an 840 micron screen, mixed with the water and sand-ground to a particle size essentially below 5 microns.

Forty-five kg. of the above composition are suspended in 200 liters of water and sprayed on a hectare of railway right-of-way. The treatment controls all vegetation for a period of one year.

EXAMPLE 9

The following slurry is prepared: 48.6 pounds of micro-milled diuron of about 97% purity is added to 431 pounds of water containing a small amount of "Tergitol" TMN as a surfactant to reduce foaming. 54.5 pounds of technical grade bromacil of about 97% purity is then added with agitation. The slurry is heated to about 85° C. and held at this temperature for 2 hours. At 45°–50° C. a marked thickening of the reaction mixture occurs indicating a considerable amount of reaction. The material is then cooled at 40°–45° C. and then filtered and dried.

Infrared scans of the material shows that the bromacil/diuron complex has been formed.

EXAMPLE 10

A formulation containing a 1:1 ratio by weight of bromacil to diuron is prepared as follows: (excess of diuron)

| Ingredients | |
|---|---|
| Bromacil/diuron complex from Example 9 | 77.4% |
| Diuron, technical | 4.6% |
| "Polyfon" H (sodium lignin sulfonate) | 3.0% |
| Basic MgCO$_3$ | 0.6% |
| "Alkanol" B (sodium alkylnaphthalene sulfonate) | 2.0% |
| Attapulgite clay | 9.8% |
| Finely divided synthetic silica | 2.6% |
| Water (1.5% of total formulation) | |

The complex is mixed in an efficient blender with the other active ingredient (excess diuron) and the wetting agent. After a uniform blend is obtained it is sprayed with water and again blended to distribute the water throughout the mixture. The other ingredients are then added and blending is continued until a uniform mixture is obtained and the mixture is then micropulverized, reblended, and sifted through a 300 micron screen and packaged.

This formulation is used to treat a railroad right-of-way and the treatment kills all vegetation along the treated area and maintains a clear right-of-way for an extended period.

EXAMPLE 11

A formulation containing a 2:1 weight ratio of bromacil to diuron (excess of bromacil) is prepared as follows:

| Ingredients | |
|---|---|
| Bromacil/diuron complex | 58.0% |
| Bromacil technical | 24.0% |
| "Polypon" H (sodium lignin sulfonate) | 3.0% |
| Basic MgCO$_3$ | 0.6% |
| Attapulgite clay | 9.8% |
| Finely divided synthetic silica | 2.6% |
| "Alkanol" B (sodium alkylnaphthalene sulfonate) | 2.0% |
| Water (1.5% of total formulation) | |

The above ingredients are blended as described in Example 10.

The resulting formulation is used to treat a railroad right-of-way and the treatment kills all vegetation along the treated area and it maintains a clear right-of-way for an extended period.

In Examples 3 to 11, inclusive, substitution of the same quantity of diuron and bromacil as found in the complexes of these examples will produce an unstable formulation which will cake or agglomerate on long term storage or in a short time under accelerated conditions at 113° F. so that the formulations are unsuitable for spray application. On the other hand the formulation of Examples 3 to 11, inclusive, containing the bromacil-diuron complex, are stable and remain so during storage.

What is claimed is:

1. A process of preparing a bromacil/diuron complex wherein the bromacil and diuron are complexed in a molar ratio of 1:1 consisting of intimately contacting the bromacil and diuron so as to allow them to react with one another and maintaining them in intimate contact with one another until substantially all of at least one of them has reacted with the other.

2. A process of claim 1 wherein the bromacil and diuron are dissolved in a common solvent and the bromacil/diuron complex is isolated.

3. The process of claim 2 wherein the bromacil/diuron complex is isolated by crystallization from a common solvent.

4. The process of claim 1 wherein the bromacil and diuron are melted together followed by solidification of the melt.

5. The process of claim 1 wherein the bromacil and diuron in finely divided form are mixed in water and heated with agitation to form the solid complex.

6. The process of claim 5 wherein the bromacil and diuron in water are heated to a temperature of at least 85° C.

* * * * *